United States Patent [19]

Penning et al.

[11] Patent Number: 5,187,187

[45] Date of Patent: Feb. 16, 1993

[54] IRREVERSIBLE LIGANDS FOR NONSTEROIDAL ANTIINFLAMMATORY DRUG AND PROSTAGLANDIN BINDING SITES

[75] Inventors: Trevor M. Penning, Springfield, Pa.; Leslie J. Askonas, Haddonfield, N.J.

[73] Assignee: Trustees of the University of Pennsylvania, Philadelphia, Pa.

[21] Appl. No.: 640,987

[22] Filed: Feb. 19, 1991

Related U.S. Application Data

[62] Division of Ser. No. 251,550, Sep. 29, 1988, Pat. No. 5,068,250.

[51] Int. Cl.$^5$ .................. C07D 209/26; A61K 31/405
[52] U.S. Cl. ..................................... 514/419; 548/492; 548/500
[58] Field of Search ................. 548/492, 500; 514/419

[56] References Cited

U.S. PATENT DOCUMENTS

| | | | |
|---|---|---|---|
| 3,778,470 | 12/1973 | Sallmann et al. | 562/454 |
| 4,166,128 | 8/1979 | Sone et al. | 562/454 |
| 4,250,192 | 2/1981 | Sallmann et al. | 560/27 |
| 4,370,486 | 1/1983 | Harnisch | 564/155 |
| 4,832,697 | 5/1989 | Rose et al. | 562/433 |
| 4,833,247 | 5/1989 | Krause | 562/433 |
| 4,859,206 | 4/1989 | Rose et al. | 562/433 |
| 4,906,662 | 3/1990 | Hashimoto et al. | 562/433 |

FOREIGN PATENT DOCUMENTS 26844 3/1972 France.
490364 8/1938 United Kingdom.

OTHER PUBLICATIONS

Penning & Talalay, *Proc. Natl. Acad. Sci. USA*, vol. 80, pp. 4504-4508 (1983).
Penning, *J. Pharm. Sci.*, vol. 74, 651-654 (1985).
Smithgall & Penning, *Biochem. Pharmacol.*, vol. 34, 831-835 (1985).
Penning et al., *Steroids* 47, 221-247 (1986).
Penning & Sharp, *Biochem. Biophys. Res. Commun.*, vol. 148, 646-652 (1987).
Kulmacz & Lands, *J. Biol. Chem.*, 260, 12572-12578 (1985).
*Chemical Abstract*, vol. 62, 16138g, Schener, 1965.
Siegal, M. I., McConnell, R. T., Porter, N. A., and Cautrecasas, P., *Proc. Natl. Acad. Sci.* USA 77, 308-312 (1980).
Vane, J. R.: Inhibition of Prostaglandin Synthesis as a Mechanism of Action for Aspirin-Like Drugs. *Nature New Biol.* 231, 232-235 (1971).
Smith, J. B. and Willis, A. L.: Aspirin Selectively Inhibits Prostaglandin Production in Human Platelets. *Nature New Biol.* 231, 235-239 (1971).
Roth, G. J., Stanford, N., Jacobs, J. W. and Majerus, P. W.: Acetylation of Prostaglandin Synthetase by Aspirin. Purification and Properties of Acetylated Protein from Sheep Vesicular Gland. *Biochemistry* 16, 4244-4248 (1977).
Roth, G. J. and Siok, C.: Acetylation of the $NH_2$-Terminal Serine of Prostaglandin Synthetase by Aspirin. *J. Biol. Chem.* 253, 3782-3784 (1978).
Van Der Ouderaa, F. J., Buytenhek, M., Nugteren, D. H. and Van Dorp, D. A.: Acetylation of Prostaglandin Endoperoxide Synthetase with Acetylsalicylic Acid. *Eur. J. Biochem.* 109, 1-8 (1980).
Rome, L. H. and Lands, W. E. M.: Structural Requirements for Time Dependent Inhibition of Prostaglandin (List continued on next page.)

*Primary Examiner*—David B. Springer
*Attorney, Agent, or Firm*—Woodcock Washburn Kurtz Mackiewicz & Norris

[57] ABSTRACT

Compounds such as 1-(4-bromoacetamidobenzyl)-5-methoxy-2-methylindole-3-acetic acid, N-(4-bromoacetamidophenyl) anthranilic acid and N-(3-bromoacetamidophenyl) anthranilic acid function as irreversible ligands for nonsteroidal antiinflammatory drug (NSAID) and prostaglandin binding sites. It is therefore expected that these compounds, and analogs thereof, will have utility as antiinflammatory drugs, as affinity labeling agents and as ligands for use in affinity chromatography.

26 Claims, 2 Drawing Sheets

OTHER PUBLICATIONS

Biosynthesis by Anti-Inflammatory Drugs. *Proc. Natl. Acad. Sci.* 72, 4863–6865 (1975).

Stanford, N., Roth, G. J., Shen, T. Y. and Majerus, P. W.: Lack of Covalent Modification of Prostaglandin Syntetase (Cyclo-Oxygenase) by Indomethacin. *Prostaglandins* 13, 669–675 (1977).

Cushman, D. W. and Cheung, H. S.: Effect of Substrate Concentration on Inhibitioin of Prostaglandin Synthetase of Bull Seminal Vesicles by Anti-Inflammatory Drugs and Fenamic Acid Analogs. *Biochem. Biophys. Acta.* 424, 449–459 (1976).

Taylor, R. J. and Salata, J. J.: Inhibition of Prostaglandin Synthetase by Tolmetin (Tolectin, McN-2559), a New Non-Steroidal Anti-Inflammatory Agent. *Biochem. Pharmacol.* 25, 2479–2484 (1976).

Smith, W. L.: Flurbiprofen-Sepharose Chromatography of the Prostaglandin Synthetase from Bovine Seminal Vesicles. *Prostaglandins* 10, 983–990 (1975).

DiPasquale, G., and Mellace, D.: Inhibition of Arachidonic Acid Induced Mortality in Rabbits with Several Nonsteroidal Anti-Inflammatory Drugs.

Smith, M. J. H.: Prostaglandins and Aspirin: An Alternative View. *Agents and Actions* 5/4 315–317 (1975).

Vargaftig, B. B.: Salicylic Acid Fails to Inhibit Generation of Thromboxane $A_2$ Activity in Platelets After In Vivo Administration to the Rat. *J. Pharm. Pharmac.* 30, 101–104 (1978).

Siegel, M. I., McConnell, R. T., and Cuatrecasas, P.: Aspirin-Like Drugs Interfere with Arachidonate Metabolism by Inhibition of 12-Hydroperoxy-5,8,10,14-Eicosatetraenoic Acid Peroxidase Activity of the Lipoxygenase Pathway. *Proc. Natl. Acad. Sci. USA* 76, 3774–3778 (1979).

Higgs, G. A., Salmon, J. A., Henderson, B., and Vane, J. R.: Pharmcokinetics of Aspirin and Salicylate in Relation to Inhibition of Arachidonate Cyclooxygenase and Anti-Inflammatory Activity. *Proc. Natl. Acad. Sci. USA* 84 1417–1420 (1987).

Winter, C. A. and Nuss, G. W.: Treatment of Adjuvant Arthritis in Rats with Anti-Inflammatory Drugs. *Arthritis and Rheumatism* 9, 394–404 (1966).

Kaltenbronn, J. S., Scherrer, R. A., Short, F. W., Jones, E. M., Beatty, H. R., Saka, M. M., Winder, C. V., Wax, J. and Williamson, W. R. N.: Structure-Activity Relationships in a Series of Anti-Inflammatory N-Arylanthranilic Acids. *Arzniem-Forsch./Drug Res.* 33, 621–627 (1983).

Penning, T. M. and Talalay, P.: Inhibition of a Major NAD(P)-Linked Oxidoreductase from Rat Liver Cytosol by Steroidal and Nonsteroidal Anti-Inflammatory Agents and by Prostaglandins. *Proc. Natl. Acad. Sci. USA* 80, 4504–4508 (1983).

Penning, T. M. and Sharp, R. B.: Prostaglandin Dehydrogenase Activity of Purified Rat Liver 3-Alpha-Hydroxysteroid Dehydrogenase. *Biochem. Biophys. Res. Commun.* 148, 646–652 (1987).

Hansen, H. S.: Inhibition by Indomethacin and Aspirin of 15-Hydroxyprostaglandin Dehydrogenase in vitro. *Prostaglandis* 8, 95–105 (1974).

Pace-Asciak, C. and Cole, S.: Inhibitors of Prostaglandin Catabolism. I. Differential Sensitivity of 9-PGDH, 13-PGR and 15-PGDH to Low Concentrations of Indomethacin. *Experientia* 31, 143–145 (1975).

Tai, H. H., Tai, C. L. and Yuan, B.: 9-Hydroxyprostaglandin Dehydrogenase from Rat Kidney. Purification to Homogeneity and Partial Characterization. *J. Biol. Chem.* 255, 7439–7443 (1980).

Hansen, H. S.: 15-Hydroxyprostaglandin Dehydrogenase. A Review. *Prostaglandins* 12, 647–679 (1976).

Magous, R., Bali, J-P., Escale, R., Girard, J-P., Rechencq, E. and Rossi, J-C.: Evidence for the Existence of High Affinity Binding Sites for Indomethacin on Human Platelets. *Mol. Pharmacol.* 29, 39–44 (1985).

Murdock, G. L., Chin, C-C., Offord, R. B., Bradshaw, R. A. and Wayrren, J. C.: Human Placental Estradiol 17B-Dehydrogenase: Identification of a Single Histidine Residue Affinity-Labeled by Both 3-Bromoacetoxyestrone and 12-Beta-Bromoacetoxy-4-Estrene-3,17-Dione. *J. Biol. Chem.* 19, 11460–11464 (1983).

Simons, S. S., Pumphrey, J. G., Rudikoff, S., Eisen, H. J.: Identification of Cysteine 656 as the Amino Acid of Hepatoma Tissue Culture Cell Glucocorticoid Receptors that is Covalently Labeled by Dexamethasone 21-Mesylate. *J. Biol. Chem.* 262, 9676–9680 (1987).

Penning, T. M., Carlson, K. E. and Sharp, R. B.: Affinity-Labelling of the Anti-Inflammatory Drug and Prostaglandin Binding Site of 3-Alpha-hydroxysteroid Dehydrogenase of Rat Liver Cytosol with 17-Beta- and 21-Bromoacetoxy-Steroids. *Biochem. J.* 245, 269–276 (1987).

Shen, T-Y, et al., (1977): Chemical and Biological Studies on Indomethacin, Sulindac and their Analogs. In: Advances in Drug Research vol. 12, (Simmonds, A. B. ed.) Academic Press, NY pp. 89–245.

IRREVERSIBLE LIGANDS FOR NONSTEROIDAL ANTIINFLAMMATORY DRUG AND PROSTAGLANDIN BINDING SITES

The Government has rights in this invention pursuant to NIH Grants GM 33464 and NRSA GM 12274, awarded by the Department of Health and Human Services.

This is a division of application Ser. No. 251,550, filed Sept. 29, 1988, now U.S. Pat. No. 5,068,250, issued Nov. 26, 1991.

BACKGROUND OF THE INVENTION

This invention relates to novel compounds which function as irreversible ligands for nonsteroidal antiinflammatory drug (NSAID) and prostaglandin binding sites.

Nonsteroidal antiinflammatory drugs are drugs of choice in the treatment of arthritis and other inflammatory disorders. It is widely accepted that NSAIDs inhibit the enzyme Prostaglandin $H_2$ synthase (PGH synthase) and prevent the synthesis of the primary prostaglandins which mediate some symptoms of inflammation. Since its introduction into the pharmaceutical market in 1963, indomethacin (I) has become the standard to which all other NSAIDs are compared.

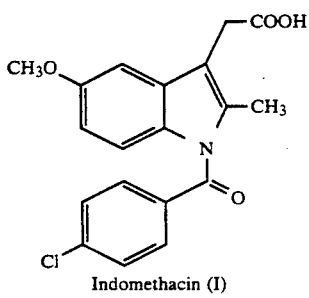

Indomethacin (I)

Another class of compounds which are equipotent with the indole acetic acids in their ability to inhibit PGH synthase are the N-phenylanthranilic acids, represented by meclofenamic acid (II) and diclofenac (III). The pyrrole acetic acids, represented by tolmetin (IV) and zomepirac (V), are slightly less potent inhibitors of PGH synthase.

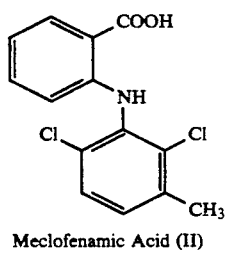

Meclofenamic Acid (II)

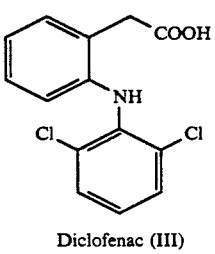

Diclofenac (III)

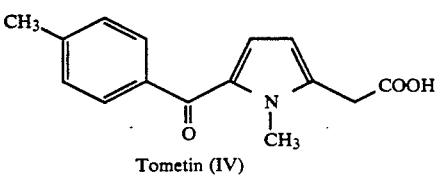

Tometin (IV)

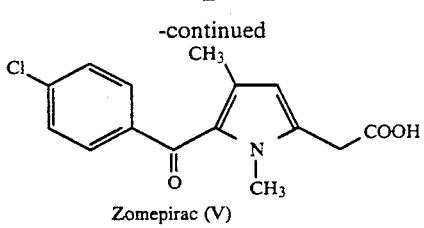

Zomepirac (V)

Although the putative target enzyme, PGH synthase, has been purified to homogeneity and its sequence deduced from its cDNA, no good topographical map of the antiinflammatory drug binding site of PGH synthase currently exists. Until antiinflammatory drug-receptor interactions are explicitly understood at the molecular level, progress in the rational design of superior drugs is hindered.

This issue is complicated by the fact that PGH synthase may not be the only target for NSAID action. Since this enzyme is not inhibited by sodium salicylate, a presumptive active ingredient of acetyl salicylate (aspirin), alternative targets for the action of NSAIDs have been proposed Prostaglandin dehydrogenases are a family of AND(P)+-linked oxidoreductases that display some regioand stereoselectivity for the oxidation of hydroxyprostaglandins. Several of these enzymes are inhibited in a reversible fashion by NSAIDs Inhibition of prostaglandin transformation at this level may contribute to the mechanism of action of NSAIDs.

Another possible target enzyme is 3α-hydroxysteroid dehydrogenase of rat liner cytosol (3α-HSD, E.C. 1.1.1.50). The homogeneous 3α-HSD of rat liver cytosol is an unusual oxidoreductase in that it will catalyze the interconversion of 3α- (axial) alcohols to ketones on the steroid nucleus, and will function as a 9, 11 and 15-hydroxyprostaglandin dehydrogenase. 3α-HSD is potently inhibited at its active site by all the major classes of NSAIDs. By virtue of its prostaglandin dehydrogenase activity, it may represent an alternative site for NSAID action. It fulfills many of the criteria expected of a target enzyme: the concentrations of drugs required to inhibit 3α-HSD are comparable to those required to inhibit PGH synthase; the rank order of inhibitory potency of NSAIDs for 3α-HSD correlates extremely well with the human dose required to produce their pharmacological effect; the enzyme can distinguish between active and inactive geometric isomers of NSAIDs. On this basis, a rapid spectrophotometric screen has been developed for the enzyme, which can be used to screen potential antiinflammatory drugs. In addition, 3α-HSD catalyzes a pro-inflammatory reaction ($PGF_{2\alpha}$ to $PGE_2$) which is blocked by NSAIDs. The indomethacin sensitive 3α-HSD is widely distributed in rat tissues, with the enzyme of highest specific activity being found in liver, then lung, testis, heart, prostate, spleen, seminal vesicle, and brain. Despite 3α-HSD's involvement in steroid hormone metabolism, the enzyme is not present in highest levels in those tissues traditionally associated with endocrine function, but is high in those that rapidly metabolize prostanoids (lung and heart). (For a Review see *Steroids*, 47, 221-247 (1986)).

Since 3α-HSD is a putative target enzyme for NSAIDs, knowledge of the topography of the enzyme's antiinflammatory drug and prostaglandin binding site could aid in future drug design. This approach may offer distinct advantages over working with PGH synthase which is difficult to assay and purify in large quantities. By contrast, 3α-HSD can be assayed spectrophotometrically, it can be purified in milligram quantities (50 mgs/purification), it has been crystallized and is undergoing x-ray diffraction analysis, and its cDNA has been cloned and is currently being sequenced.

One method of mapping the antiinflammatory drug binding site of 3α-HSD is by synthesizing affinity labeling analogs of NSAIDs, i.e. acylating agents. Affinity labeling analogs of substrates and inhibitors of hydroxysteroid dehydrogenases (HSDs) have been widely used to characterize steroid binding sites. (*J. Biol. Chem.*, 247, 3424–3433 (1972); *J. Biol Chem.*, 250, 7656–7662 (1975)). Indeed, bromoacetoxy analogs of dihydrotestosterone and desoxycorticosterone have been used to characterize the steroid binding domain of 3α-HSD. In this instance, attack of radiolabeled bromoacetoxy steroids by an enzyme nucleophile leads to the formation of covalently modified enzyme. Upon complete acid hydrolysis of the inactivated 3α-HSD, the steroid is released as the free alcohol, leaving behind a radiolabeled carboxymethylated amino acid which was identified as a carboxymethyl cysteine from its elution position on an amino acid analyzer. Furthermore, enzymatic digestion of the inactivated radiolabeled enzyme has lead to the purification and partial sequence of active site peptides.

have been typically used for kinetic analyses NSAIDs are known to inhibit only the cyclooxygenase portion of the enzyme's activity, and it is this function which has been attributed to their overall effect. PGH synthase has been purified to homogeneity from ovine and bovine seminal vesicles and the amino acid sequence deduced from its cloned cDNA. Extensive kinetic characterization has shown that the enzyme can catalyze its self destruction in the presence of its substrates (arachidonic acid and $O_2$), presumably by a free radical mechanism. Kinetic studies of the inhibition of PGH synthase by NSAIDs have suggested that although these drugs are competitive with arachidonic acid, they may also bind to a second site. NSAIDs are also capable of promoting self destruction of PGH synthase, although a covalent complex has never been isolated. In contrast, the methyl esters of NSAIDs bind reversibly to the PGH synthase active site and do not promote self destruction of the enzyme. Despite these studies, the topography of the NSAID binding site has remained poorly defined. Through the use of affinity labeling analogs of NSAIDs described herein, amino acids involved in NSAID binding could be identified, active site peptides could be purified and sequenced, and the position of the active site could be deduced from the sequence of the cDNA clone. This knowledge would greatly aid in the future design of NSAIDs.

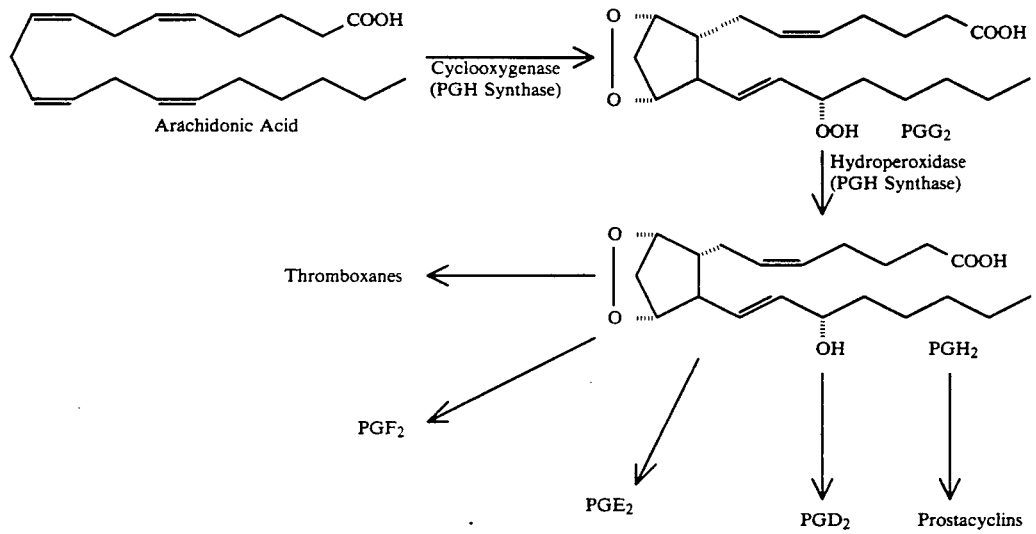

Scheme A

In a similar study, mesylate analogs of dexamethasone have been used to identify amino acids and peptides involved in steroid binding to the glucocorticoid receptor (*J. Biol. Chem.*, 262, 9669–9675, (1987); *J. Biol. Chem.*, 263, 6842–6846 (1988)).

The use of affinity labeling analogs as inhibitors of HSD's and steroid receptors has proven useful in understanding the topography of these steroid binding sites. Application of this method to the NSAID and prostaglandin binding sites of 3α-HSD, prostaglandin dehydrogenases, and PGH synthase would be expected to reveal similar information and aid in the understanding of binding of NSAIDs to these sites.

Prostaglandin $H_2$ Synthase (PGH synthase, E.C. 1.14.99.1) is a dual function enzyme, catalyzing the cyclooxygenation of arachidonic acid to $PGG_2$, and its further peroxidation to $PGH_2$ (Scheme A). It has been studied in a variety of tissues, but the seminal vesicles In addition to PGH synthase, indomethacin and other NSAIDs have been shown to inhibit at low concentrations several prostaglandin dehydrogenases. They inhibit the action of 15-hydroxyprostaglandin dehydrogenase involved in the conversion of $PGE_2$ to 15-keto-$PGE_2$. NSAIDs also inhibit 13,14-prostaglandin reductase and 9-hydroxyprostaglandin dehydrogenase activities. Affinity labeling analogs based on NSAIDs have the capability of mapping the topography of the active site of these enzymes.

Affinity labeling analogs of NSAIDs also have the potential to act as ligands for affinity chromatography and would aid in the purification of PGH synthase, prostaglandin dehydrogenases and NSAID receptors and binding sites. Indeed, flurbiprofen (a NSAID) has been used as a ligand for affinity chromatography in the purification of PGH synthase. After initial solubilization, the enzyme is passed over an affinity column, in which flurbiprofen was attached to CNBr activated Sepharose 4B through a 3,3'-diaminodipropylamine side arm. PGH synthase activity was retarded, but could not be eluted in a specific manner by NSAIDs. Elution from the column was not improved by substituting more potent NSAIDs. Elution could be achieved by high salt in the absence of NSAIDs or by flufenamic acid, to give a 15-fold enrichment of the PGH synthase activity (*Prostaglandins*, 10, 983–990, (1975)). This method of flurbiprofen affinity chromatography has not been used routinely in published purification procedures for the synthase. Coupling of the affinity labeling NSAID analogs described herein to a suitably activated solid matrix support such as glass, silica, agarose, sepharose, etc., as could be achieved through methods known in the art, would be expected to provide a substantial improvement in affinity chromatography, since the corresponding parent NSAIDs have a greater affinity for PGH synthase than flurbiprofen. Many enzymes and receptors are commonly purified through the use of competitive ligands bound to affinity resins. This method can greatly reduce the number of steps and time involved in their purification. (For general reviews see *J. Biol. Chem.*, 245, 3059 (1970), and Venter and Harrison, Eds., "Receptor Purification Procedures" in Receptor Biochemistry and Methodology (Alan R. Liss, New York, 1984), the disclosures of which are hereby incorporated by reference).

Affinity labeling agents based on the potent NSAIDs described herein also have the potential to act as pro-drugs. It is generally accepted that aspirin (acetyl salicylate) is rapidly de-acetylated *in vivo* by plasma esterases to yield free salicylate. The plasma t½life of aspirin is 15 minutes. In the treatment of arthritis it is the plasma level of salicylate that is the indicator of therapeutic efficacy. Slow hydrolysis of bromoacetylated analogs of indomethacin, N-phenylanthranilic acids and tolmetin analogs may prolong the half-life of the active drug in the treatment of the arthritic. Some of the therapeutic efficacy of aspirin has also been attributed to its irreversible acetylation of PGH synthase (e.g. platelet PGH synthase). Since the bromoacetylating agents described herein could also irreversibly inactivate PGH synthase in vivo, they may represent superior "aspirin-like" drugs.

Therefore, the affinity labeling analogs of NSAIDs described herein could have a number of utilities: (a) they may act as affinity labeling agents of putative target enzymes e.g. 3α-HSD/PGH synthase and prostaglandin dehydrogenases, and permit the topography of the NSAID binding site to be mapped; (b) they may act as affinity ligands on immobilized supports for the purification of prostaglandin transforming enzymes and NSAID receptors; (c) by de-acetylation they may act as pro-drugs and (d) by acetylating PGH synthase in vivo they may act as superior "aspirin-like" drugs.

SUMMARY OF THE INVENTION

Tests by the inventors indicate that novel compounds of the formulae (VI), (VII) and (VIII) are irreversible ligands for the NSAID binding site of 3α-HSD:

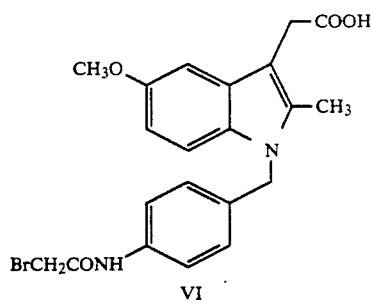

VI

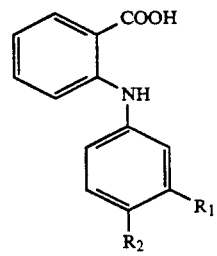

VII: $R_1$ = H and $R_2$ = NHCOCH$_2$Br
VIII: $R_1$ = NHCOCH$_2$Br and $R_2$ = H Compounds of formulae (VI), (VII) and (VIII) irreversibly inactivate 3α-HSD in a time and concentration dependent manner, as illustrated in Scheme B with compound (VI). Active enzyme cannot be regenerated by extensive dialysis or gel filtration chromatography, indicating that an irreversible process has occurred. In addition, under initial velocity conditions, these compounds are competitive inhibitors of 3α-HSD with respect to androsterone. Since all the NSAIDs are competitive with this steroid, this data would suggest that the compounds (VI–VIII) and analogs thereof affinity label the steroid/NSAID binding domain.

Scheme B

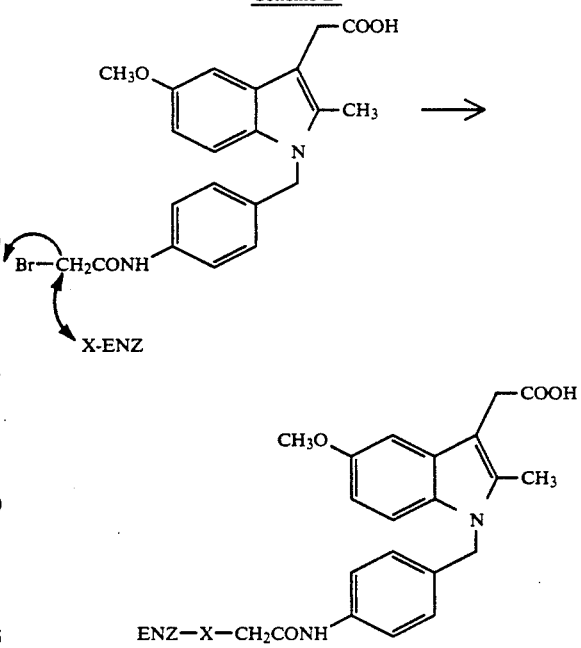

(X = any nucleophilic amino acid residue on the enzyme, ENZ)

This invention therefore relates to the novel compounds of formulae (i), (ii) and (iii). This invention further relates to methods of inactivating a NSAID or prostaglandin binding sites selected from, but not limited to 3α-HSD, prostaglandin synthase and prostaglandin dehydrogenases comprising said binding sites, with at least one of the compounds of formulae (i), (ii) and (iii). Still further, this invention relates to the use of compounds of formulae (i), (ii) and (iii) as ligands for affinity chromatography and drugs or pro-drugs in pharmaceutical compositions.

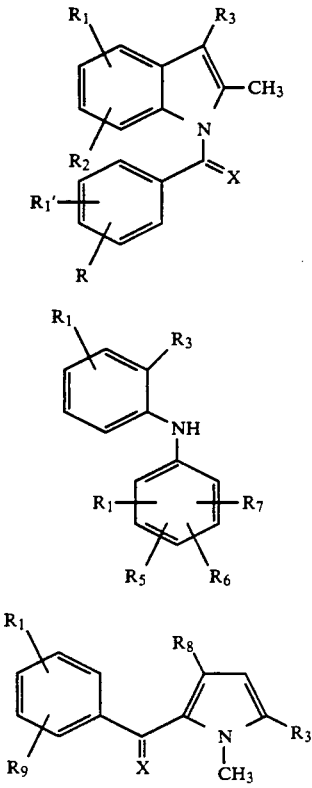

where
X is $H_2$ or O;

$R_1$ is selected from the groups consisting of H, $NHCOCH_2Z$, $OCOCH_2Z$, $COCH_2Z$, $CH_2N_3$, and $CH_2OSO_2Me$;

$R_2$ is selected from the groups consisting of H, OMe, $N(Me)_2$, $NO_2$, $NH_2$, OH, Z, $CH_3$, $CH_2Z$, $CHZ_2$, and $CZ_3$;

$R_3$ is selected from the groups consisting of Y, $CH_2Y$, $CH(CH_3)Y$ and Y is selected independently from the groups consisting of COOH, COOMe, COOEt, $CH_2O$-$COCH_2Z$, $CH_2NHCOCH_2Z$, $CH_2N_3$, $CH_2OSO_2Me$, and $COCH_2Z$;

$R_4$ is selected from the groups consisting of H, Z, $SCH_3$, $S(O)CH_3$, $NO_2$, $NH_2$, OH, $CH_3$, $CH_2Z$, $CHZ_2$, and $CZ_3$;

$R_5$, $R_6$, and $R_7$ are selected independently from the groups consisting of H, Z, $CH_3$, $CH_2Z$, $CHZ_2$, $CZ_3$, $NO_2$, $NH_2$, and OH;

$R_8$ is selected from H and $CH_3$;

$R_9$ is selected from the groups consisting of H, Z, $NO_2$, $NH_2$, OH, $CH_3$, $CH_2Z$, $CHZ_2$, and $CZ_3$;

where Z is a halogen atom;

provided that for compounds of formulae (i) and (ii), if $R_1$=H in both rings, Y is other than COOH, COOMe or COOEt; and if Y= COOH, COOMe, or COOEt, $R_1$ is other than H in both rings;

provided that for compounds of formula (iii), if $R_1$=H, Y is other than COOH, COOMe or COOEt; and if Y =COOH, COOMe or COOEt, $R_1$ is other than H.

Still further, this invention relates to pharmaceutical compositions and affinity resins synthesized from compounds comprising one of the compounds of formulae (i), (ii) and (iii) above.

DETAILED DESCRIPTION OF THE INVENTION

Use of the Compounds

Studies show that compounds of formulae (I) through (VIII) are competitive inhibitors of androsterone (3α-hydroxysteroid) oxidation catalyzed by 3α-HSD, as shown by the example of compound (VII) in FIG. 1. Inhibition constants ($K_i$'s) determined under initial velocity conditions by the method of Dixon (Biochem. J., 55, 170–171, (1953)) are shown in Table 1:

TABLE 1

| Compound | $K_i$ |
|---|---|
| Indomethacin (I) | 0.835 μM |
| Meclofenamate (II) | 1.10 μM |
| Tolmetin (IV) | 29 μM |
| Compound (VI) | 15 μM |
| Compound (VII) | 2.5 μM |
| Compound (VIII) | 1.5 μM |

Figure 2A:
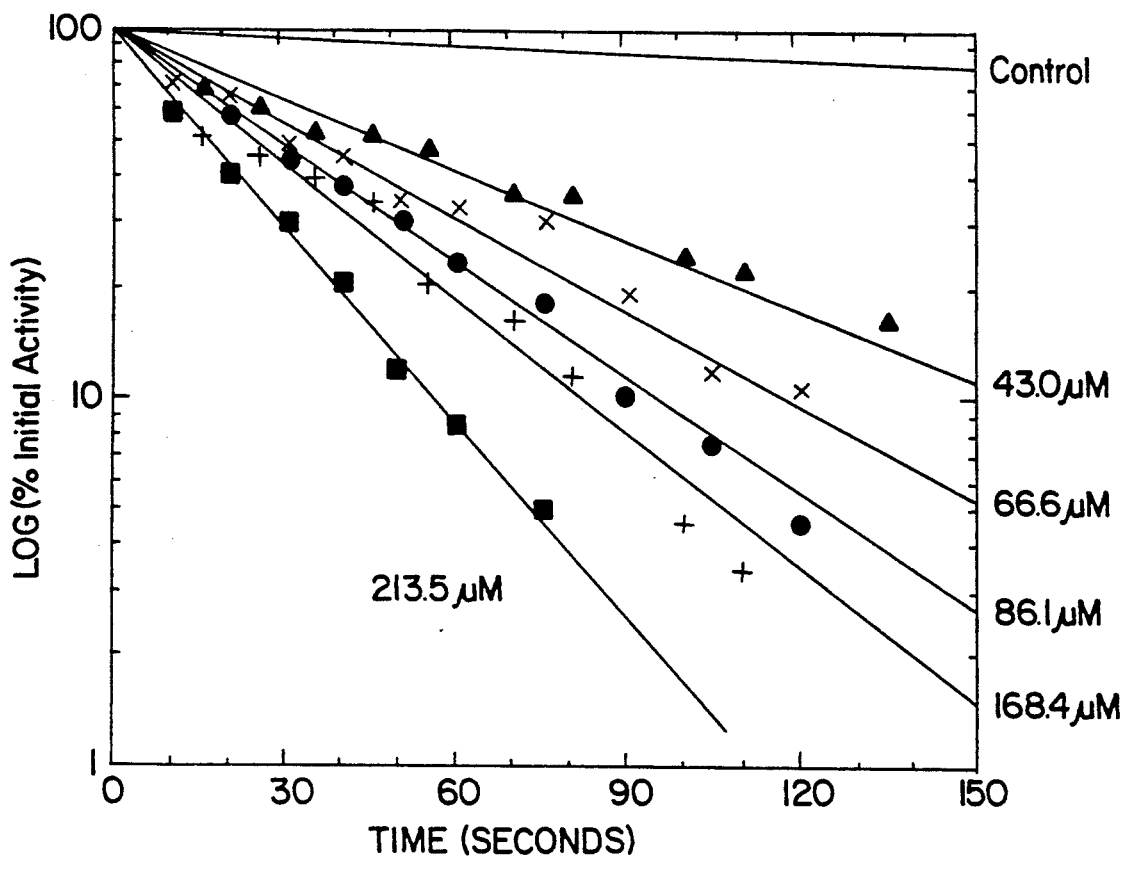
FIGS. 2a and 2b are plots showing the time and concentration dependent inactivation of 3α-HSD by compound (VII).
Figure 2B:
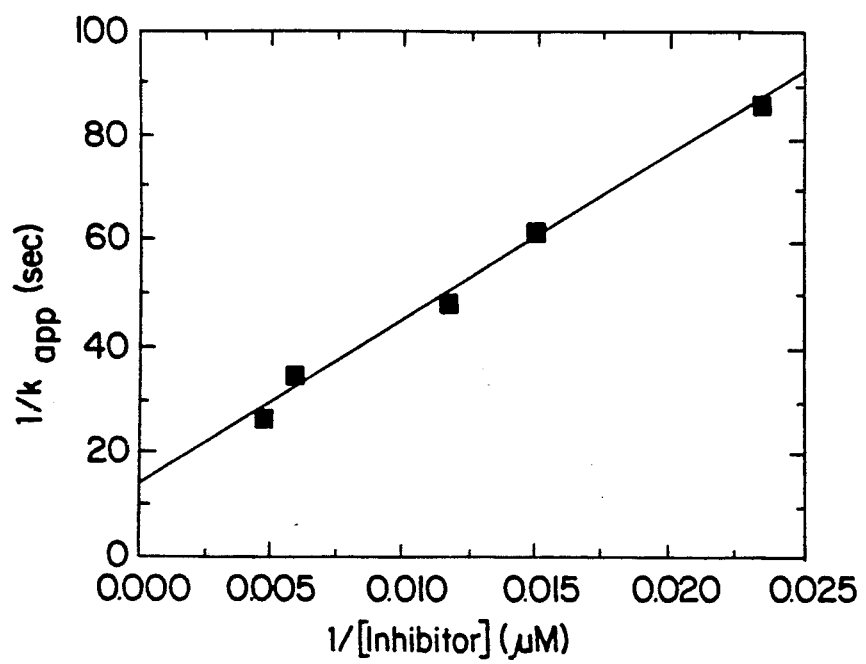

In addition, compounds of the formulae (VI), (VII) and (VIII) cause time and concentration dependent loss of 3α-HSD activity as shown in FIG. 2a for the compound (VII). Analysis of this data by the method of Kitz and Wilson (J. Biol. Chem., 237, 3245–3249 (1962)) leads to an independent determination of the $K_i$, and to a measurement of a t½life for the enzyme at saturating inactivator concentrations. For compound (VI), this analysis yields a $K_i$ of 233 μm and a t½of 40.2 sec. For compound (VII), $K_i$ is determined to be 161 μm with a t½of 12.1 sec (FIG. 2b). Finally, for compound (VIII), $K_i$ was determined to be 155 μm with a t½of 7.1 sec. The difference in the $K_i$'s determined from the two methods can probably be attributed to the difference in the binding order in the enzymatic mechanism. The activity of enzyme inactivated by compounds of formulae (VI), (VII) and (VIII) cannot be returned by extensive dialysis, suggesting that a stable covalent bond has formed.

Compounds of formulae (i), (ii) and (iii) are useful as affinity labeling agents. Attack of these analogs by an enzyme nucleophile (Scheme B) can lead to a covalently labeled amino acid. Upon complete acid hydrolysis of the inactivated enzyme, the carboxymethylated amino acid can be readily identified by its elution position on an amino acid analyzer. In addition, if the affinity labeling function has been labeled with radioactivity, the radiolabeled amino acid can be detected in the effluent fractions of the amino acid analyzer. Identification of the amino acids that are important in the binding of NSAIDs and prostaglandins is an important first step in using this enzyme as a model for drug design. Furthermore, enzymatic digestion of the inactivated radiolabeled enzyme could lead to identification of the peptides involved in NSAID binding. Computer modeling of these peptides along with the drugs which they bind may aid the development of antiinflammatory drug design.

Extension of these affinity labeling studies to PGH synthase should provide similar information. By inactivating PGH synthase with a radiolabeled NSAID analog, the peptides involved in antiinflammatory drug binding to PGH synthase may be isolated and sequenced. By cross-referencing the sequence of the isolated peptides with the sequence deduced from its cDNA, the antiinflammatory drug binding site of PGH synthase can be more clearly defined. This knowledge would aid greatly in the further development of NSAIDs In addition, this invention covers the use of compounds of formulae (i), (ii) and (iii) as ligands for affinity resins. The coupling of activated affinity resins to compounds of formulae (i), (ii) and (iii) could lead to resins capable of substantially simplifying the purification of NSAID and prostaglandin binding sites, including but not limited to 3α-HSD, NSAID binding sites, prostaglandin dehydrogenases and PGH synthase.

The activity of the novel compounds of formulae (i), (ii) and (iii) as irreversible ligands for 3α-HSD suggests that these compounds could be used in pharmaceutical compositions useful as antiinflammatory drugs. This invention, therefore, further relates to pharmaceutical compositions comprising an effective antiinflammatory amount of one or more compounds of formulae (i), (ii), and (iii), or pharmaceutically acceptable salts thereof, in combination with any of the conventional pharmaceutically acceptable carriers or diluents. Suitable pharmaceutical carriers are well known in the art and described, for example, in Remington's Pharmaceutical Sciences, E. W. Martin, a standard reference text in this field. Pharmaceutically acceptable salts include, but are not limited to, salts of hydrochloric, hydrobromic, sulfuric, benzenesulphonic, acetic, fumaric, oxalic, malic and citric acids, as well as hydroxides of potassium and sodium. An effective antiinflammatory dose of the compounds of the invention would vary from compound to compound and patient to patient, but it is expected that such a dose would be in the range of about 0.001 to 100 mg/kg.

Preparation of the Compounds

Compounds of formula (i) can be synthesized by either one of three published methods. The first method, outlined in Scheme C, involves a Fischer indole coupling of a substituted phenylhydrazine with levulinic acid or its ester. Coupling between the substituted indole and an appropriately substituted benzoyl chloride yields compounds of formula (i) or their immediate precursors (*J. Amer. Chem. Soc.*, 85, 488–489, (1963)).

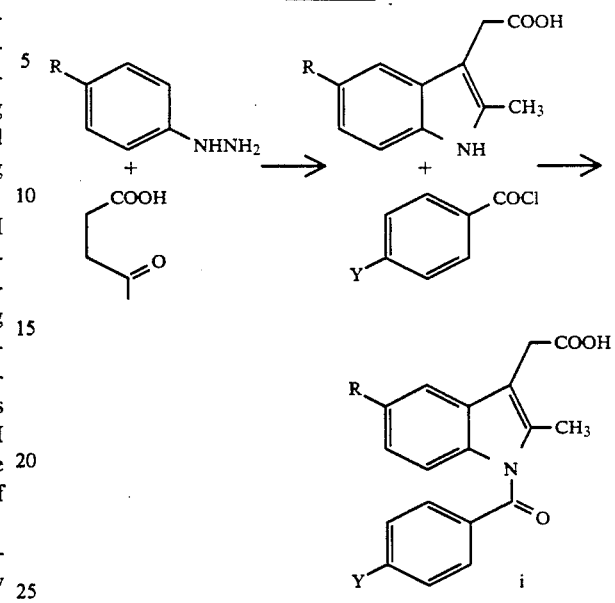

The second method utilizes a modification of this method, as shown in Scheme D. Reaction of a substituted arylhydrazine with acetaldehyde or benzaldehyde forms the $N^2$-hydrazone, which is subsequently benzoylated at the $N^1$-position with an appropriately substituted benzoyl chloride. Acid hydrolysis of the hydrazone to yield the free amine is followed by reaction with levulinic acid under Fischer indole synthesis conditions, to yield compounds of formula (i) or their immediate precursors (*Chem. Pharm. Bull.*, 16, 647–653 (1968)).

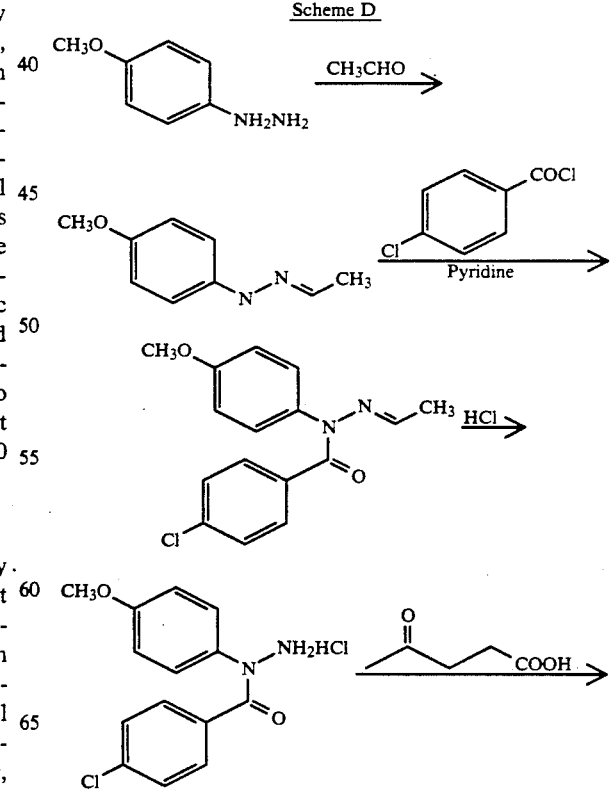

-continued
Scheme D

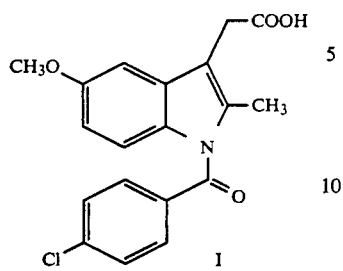

-continued
Scheme E

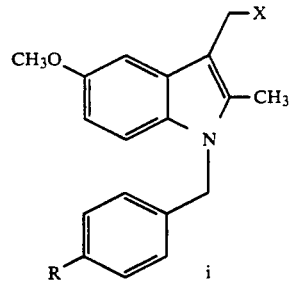

Finally, compounds of formula (i) may be synthesized as outlined in Scheme E. A substituted aniline is coupled with an appropriately substituted benzoyl chloride to yield the benzanilide derivative. Reaction of this substituted benzanilide with NaH followed by but-2-ynyl bromide forms the n-but-2-ynyl-substituted benzanilide. Reduction of the anilide with 1:1 lithium aluminum hydride and aluminum chloride affords the benzyl intermediate. N-oxidation with m-chloroperbenzoic acid, consecutive sigmatropic rearrangements, ketalization, and attack by an appropriate nucleophile yields the substituted N-benzyl indole (*Chem. Pharm. Bull.*, 24, 770-777 (1976)).

Using NaCN as the attacking nucleophile (X⁻) with subsequent base hydrolysis will yield the acid or corresponding ester, while the use of NaN$_3$ would result in azide formation. To synthesize compound (VI), anisidine and p-nitrobenzoyl chloride are the appropriate starting materials. Reduction of the p-nitro group to the amine, followed by reaction with bromoacetic anhydride leads to the synthesis of compound (VI), as shown in Scheme F.

Scheme E

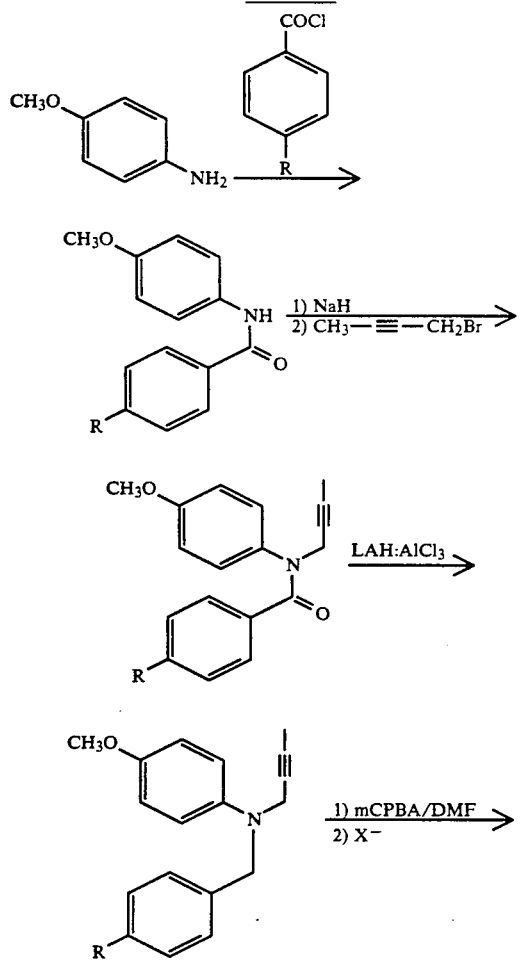

Scheme F

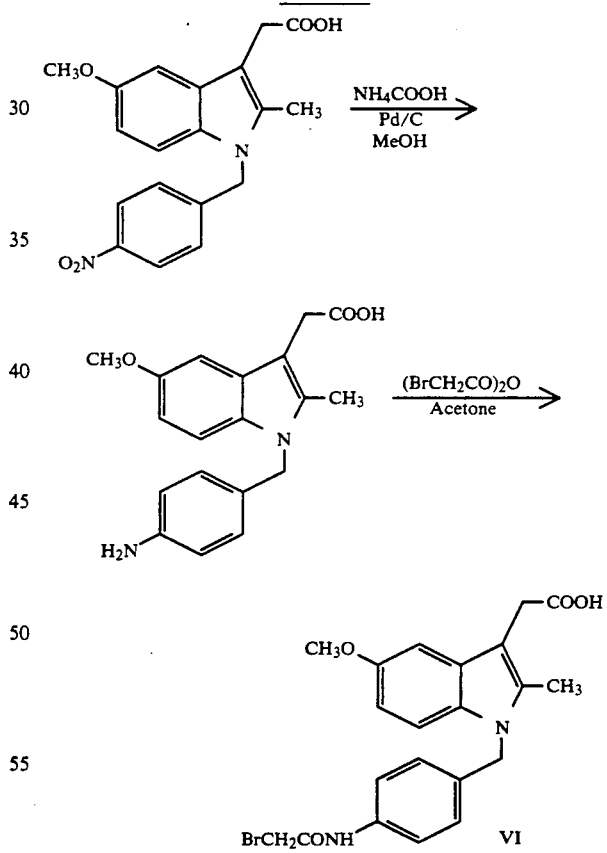

Compounds of formula (ii) can be prepared by use of the Ullmann reaction, as shown in Scheme G. (For reviews see Acheson, "Acridines" in The Chemistry of Heterocyclic Compounds (Interscience, New York, 1956); Albert, "The Acridines" (Edward-Arnold Co. London, 1951)). Diphenyliodonium-2-carboxylate (DPIC) is synthesized by oxidation of o-iodobenzoic acid and subsequent reaction with benzene. Coupling of the DPIC with an appropriately substituted aniline derviative in the presence of catalytic copper yields N-phenylanthranilic acid (Scheme G(a)) (*J. Org. Chem.,* 45, 2127–2131 (1980)). Schemes G(b) and G(c) are alternative methods for synthesis of compounds of general formula (ii). Since these three methods are largely complimentary in the substitutions they allow, diverse functionalities may be incorporated into the N-phenylanthranilic acid nucleus (Scheme G).

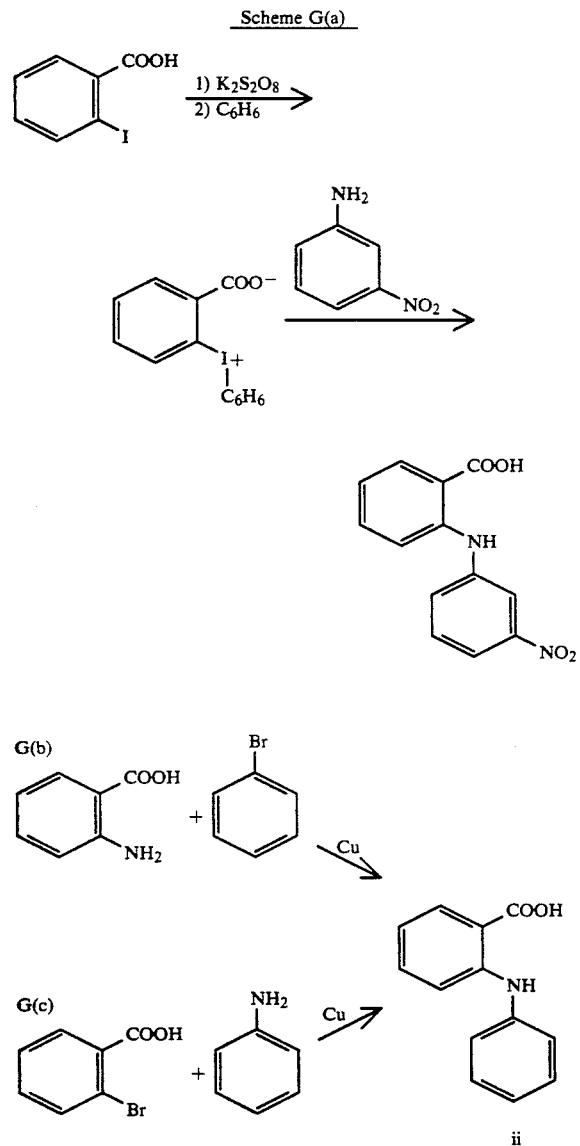

Compounds of formula (iii) can be synthesized by modification of published procedures (Scheme H). l-Methylpyrrole-2-acetonitrile can react under Friedel-Crafts aroylation conditions with a substituted aroyl halide, which can then be saponified to the free acid. By varying the initial pyrroles and aroyl halides, a variety of compounds of formula (iii) can be synthesized (*J. Med. Chem.,* 14 646–647 (1971); *J. Med. Chem.,* 16, 172–174 (1973)).

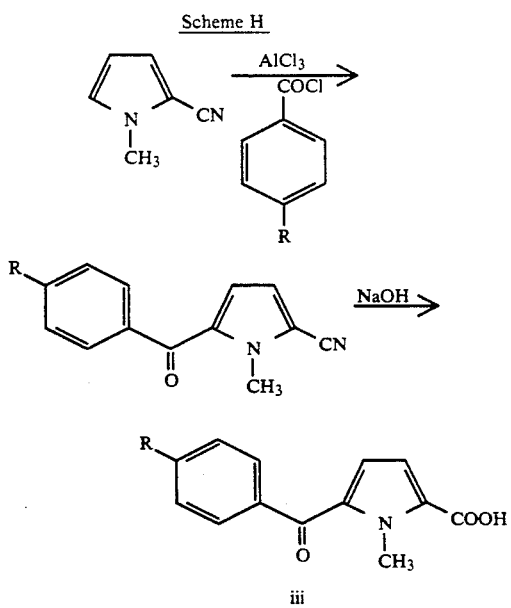

Coupling of compounds of the general formulae (i), (ii) and (iii) as ligands for affinity chromatography will be accomplished by standard methods. Suitable solid matrix supports, activation methods, and side arms are well known in the art and described, for example, in Affinity Chromatography, P. Mohr and K. Pommerening (Marcel Dekker, Inc., New York, 1985), a standard reference in the field. Solid matrix supports, include, but are not limited to, derivatives of agarose, dextran, cellulose, polyacrylamide, polystyrene, porous glass, and silica. Suitable spacer arms include, but are not limited to derivatives of diaminoalkanes, hydroxyalkyl methacrylate, aminocarbonic acids, and aminoalkylalcohols.

The preparation of the compounds of this invention will be further illustrated by the following examples.

EXAMPLE 1

Preparation of 1-(4-bromoacetamidobenzyl)-5-methoxy-2-methylindole-3-acetic acid (VI)

1-(4-Nitrobenzyl)-5-methoxy-2-methylindole-3-acetonitrile was synthesized as described, substituting p-nitrobenzoyl chloride for benzoyl chloride (*Chem. Pharm. Bull.,* 24, 770–777 (1976)).

The nitrobenzyl indole acetonitrile (150 mg, 0.45 mmol) was combined with 80 mg 10% pd/C and 230 mg ammonium formate (8 eq, 3.6 mmol) in 5 ml MeOH and refluxed under nitrogen for 4 hours. The mixture was cooled, and the Pd/C removed by filtration through a celite pad. After removal of the solvent in vacuo, the residue was suspended in acetone and excess ammonium formate filtered off. After concentration of the acetone solution, the crude amine was purified by preparative silica TLC (7% acetone in chloroform), and crystallized from MeOH to yield 1-(4-aminobenzyl)-5-methoxy-2-methylindole acetonitrile (112 mg, 0.37 mmol, 82% yield). N.m.r.:δ (p.p.m.) ([$^2$H]chloroform), 2.27 (3H, s, 2-CH$_3$), 3.1 (2H, broad s, NH$_2$, D$_2$O exchangeable), 3.7 (2H, s, CH$_2$-CN), 3.87 (3H, s, OCH$_3$), 5.07 (2H, s, N-CH$_2$-φ), 6.4–7.2 (7H, multiplets, aryl protons). U.V. maxima, 206 nm, $\epsilon_{206}$=51,300 M$^{-1}$, cm$^{-1}$, 225 nm, $\epsilon_{225}=37,300$ M$^{-1}$ cm$^{-1}$, 281 nm, $\epsilon_{281}=14,500$ M$^{-1}$ cm$^{-1}$.

The aminobenzyl indole acetonitrile (48 mg, 0.16 mmol) was combined with three equivalents of 1N NaOH (471 μl, 0.47 mmol) in 2 ml EtOH and allowed to reflux for 18 hours. The product was isolated by evaporating the solution to dryness in vacuo, dissolving the product in acetone and filtering off excess sodium hydroxide. The amino acid was then used immediately without further purification for the next step.

4-Aminobenzyl indole acetic acid (66 mg, 0.2 mmol) was dissolved in 3 ml dry acetone, and to this solution bromoacetic anhydride (53 mg, 0.2 mmol) was added. The reaction vial was sealed and the solution allowed to stir for one hour at room temperature. At the end of this period, the solution was concentrated under a gentle stream of nitrogen, and the precipitated product filtered and allowed to air dry. The resulting product was then crystallized from 90% EtOH to yield 1-(4-bromoacetamidobenzyl)-5-methoxy-2-methylindole-3-acetic acid (VI). N.m.r.: δ (p.p.m.) ([$^2$H]acetone), 2.3 (3H, s, 2-CH$_3$), 3.4 (2H, s, CH$_2$—COOH), 3.75 (3H, s, OCH$_3$), 4.0 (2H, s, COCH$_2$Br), 5.3 (2H, s, N-CH$_2$-φ), 6.65-7.5 (7H, multiplets, aryl protons). U.V. maxima, 201 nm, $\epsilon_{201}=43,800$ M$^{-1}$ cm$^{-1}$, 227 nm, $\epsilon_{227}=28,800$ M$^{-1}$, cm$^{-1}$, 279 nm, $\epsilon_{279}=14,800$ M$^{-1}$ cm$^{-1}$.

EXAMPLE 2

Preparation of N-(4-bromoacetamidophenyl) anthranilic acid (VII).

N-(4-Nitrophenyl) anthranilate was synthesized as described using p-nitroaniline (*J. Org. Chem.*, 45, 2127-2131 (1980)).

4-Nitro-N-phenylanthranilate (500 mg, 1.94 mmol) was dissolved in 8 ml EtOH with stirring, 5 equivalents SnCl$_2$ added, and the mixture heated to reflux. After 8-12 hours the reaction was judged to be complete by TLC monitoring (3:7:0.1; EtOAc, CHCl$_3$, AcOH); the reaction mixture was filtered through celite, and the solvent removed in vacuo. The residue was taken up in 100 ml each EtOAc and saturated NaHCO$_3$, and the aqueous solution extracted twice more with EtOAc. The organic phases were combined, washed with 100 ml saturated NaCl solution, dried over MgSO$_4$, and the drying agent removed by filtration. After evaporation of the solvent, the product was used immediately in the next reaction. If left to expose to oxygen and light, the product rapidly discolored.

The aminophenyl anthranilate (50 mg, 0.219 mmol) was dissolved in DMF (distilled from CaH$_2$) and 1.2 equivalents of bromoacetic anhydride added. After stirring for 30 minutes at room temperature in a closed flask, the product was slowly precipitated by the addition of 2 volumes of water. Continued stirring for 15 minutes was followed by filtration of the product. The resulting N-(4-bromoacetamidophenyl)anthranilic acid (VII) could then be crystallized from EtOH/water. N.m.r.: δ(p.p.m.) ([$^2$H]acetone), 4.03 (2H, s, COCH$_2$Br), 6.8-8.8 (8H, m, aryl protons). U.V. maxima, 218.5 nm, $\epsilon_{218.5}=26,800$ M$^{-1}$ cm$^{-1}$, 299 nm, $\epsilon_{299}=18,600$ M$^{-1}$ cm$^{-1}$, 355 nm, $\epsilon_{355}=10,700$ M$^{-1}$ cm$^{-1}$.

EXAMPLE 3

Preparation of N-(3-bromoacetamidophenyl) anthranilic acid (VIII)

Compound (VIII) was synthesized exactly as described in example 2, except the synthesis utilized m-nitroaniline as the starting material. U.V. maxima, 222.5 nm, $\epsilon_{222.5}=21,400$ M$^{-1}$ cm$^{-1}$, 287 nm, $\epsilon_{287}=13,500$ M$^{-1}$ cm$^{-1}$, 352 nm, $\epsilon_{352}=6,600$ M$^{-1}$ cm$^{-1}$.

FIGURE LEGENDS

Figure 1A:
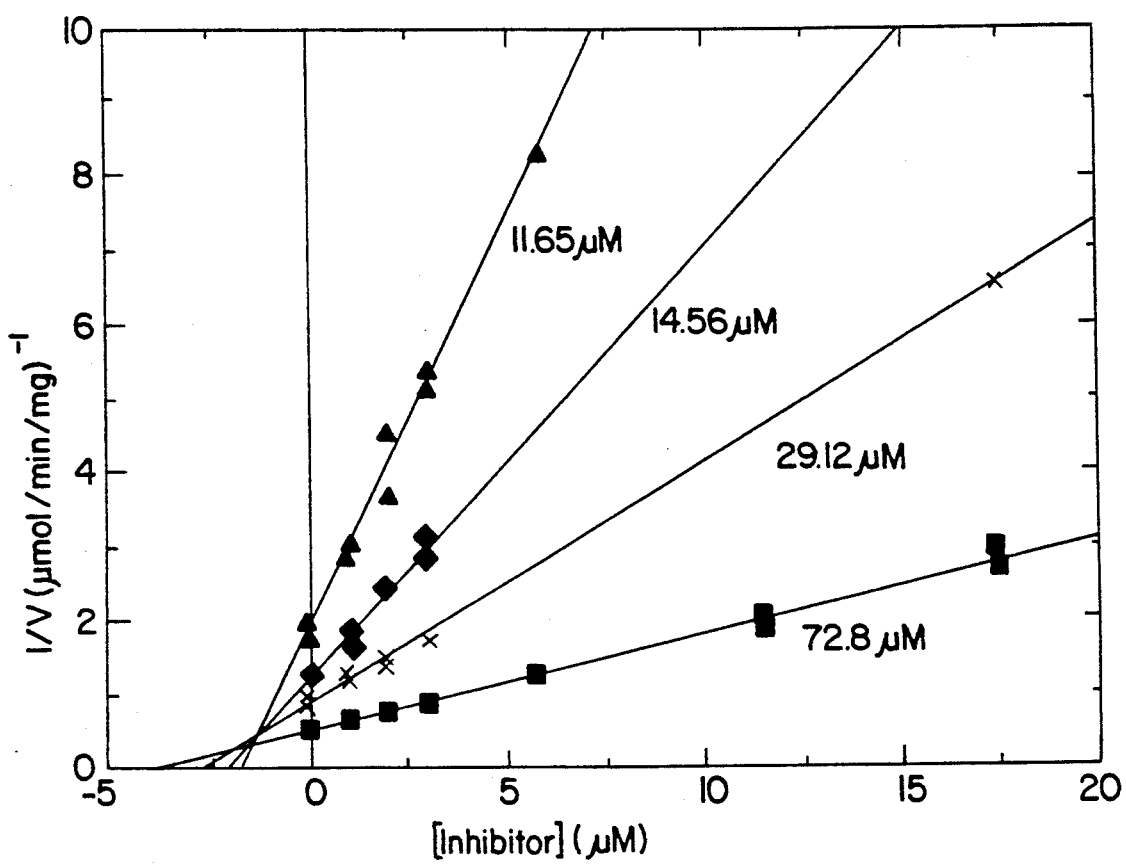
FIGS. 1a and 1b are plots showing the competitive nature of compound (VII) with respect to androsterone oxidation.
Figure 1B:
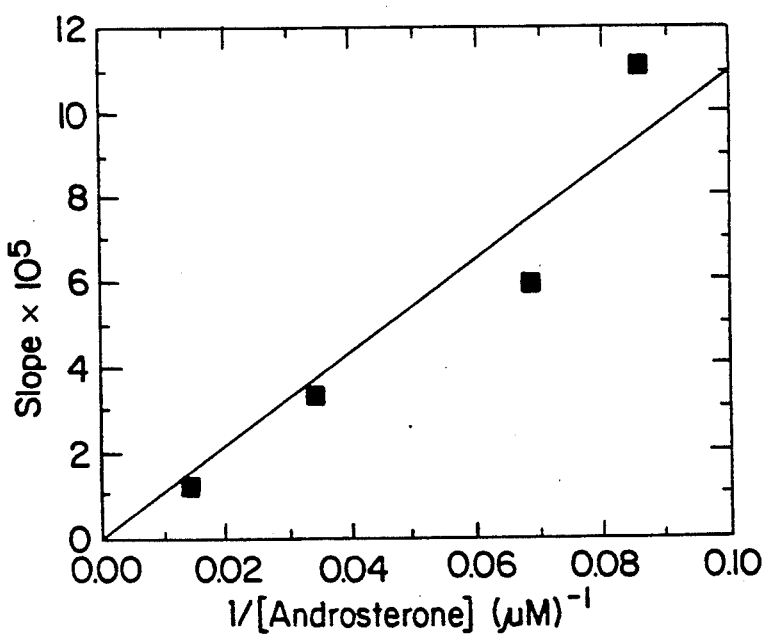

FIG. 1 shows the competitive inhibition of 3α-HSD by the compound of formula (VI). Initial velocities of androsterone oxidation Were measured at fixed substrate concentrations (11-75 μM) while the concentrations of the compound of formula (VII) (0-20 μM) were varied. Initial rates were determined spectrophotometrically by measuring the rate of NADH formation at 340 nM over 5 minutes in an assay containing 2.3 mM AND$^+$ in 0.1 M potassium phosphate buffer pH 7.0, with 4% acetonitrile (v/v) as a cosolvent in a 1 ml system. The assay was started by the addition of enzyme. The slope of the resulting lines of FIG. 1a were replotted in FIG. 1b against the inverse of the corresponding androsterone concentration. From the slope of this plot, the $K_i$ was determined.

FIG. 2 shows the time and concentration dependent inactivation of 3α-HSD by the compound of formula (VII). Inactivation of 3μ-HSD (15 μM) was conducted in incubations (50 μl) of 10 mM potassium phosphate buffer pH 7.0 containing 1 mM EDTA and 4% acetonitrile as a cosolvent. Enzyme activity was followed over time by diluting an aliquot of the incubation mixture in a 1 ml assay containing 2.3 mM AND$^+$ and 75 μM androsterone in 0.1 M potassium phosphate buffer, pH 7.0 containing 1 mM mercaptoethanol, with 4% acetonitrile as a cosolvent. Initial rates were determined as described in FIG. 1. Because of the 100 fold or greater dilution of the enzyme into the assay, the initial rate measured is an indication of the enzyme activity remaining at that time. Initial rates of inactivation ($k_{app}$'s) were determined from semilogarithmic plots of percent enzyme activity remaining versus time. Data was replotted (FIG. 2b) as $1/k_{app}$ vs 1/[Inhibitor] from which $k_{inact}$ (the rate constant for enzyme inactivation) and $K_i$ (the binding constant for compound (VII)) were determined.

What is claimed is:
1. A compound of the formula

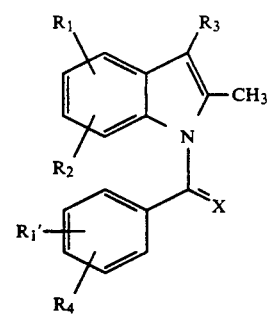

where
X is H$_2$ or O;
R$_1$ and R$_1'$ are independently selected from the groups consisting of H, NHCOCH$_2$Z, OCOCH$_2$Z, COCH$_2$Z, CH$_2$N$_3$, and CH$_2$OSO$_2$Me;
R$_2$ is selected from the groups consisting of H, OMe, N(ME)$_2$, NO$_2$, NH$_2$, OH, Z, CH$_3$, CH$_2$Z, CHZ$_2$, and CZ$_3$;
R$_3$ is selected from the groups consisting of Y, CH$_2$Y, CH(CH$_3$)Y and Y is selected independently from the groups consisting of COOH, COOMe, COOEt, $CH_2OCOCH_2Z$, $CH_2NHCOCH_2Z$, $CH_2N_3$, $CH_2OSO_2Me$, and $COCH_2Z$;

$R_4$ is selected from the groups consisting of H, Z, $SCH_3$, $S(O)CH_3$, $NO_2$, $NH_2$, OH, $CH_3$, $CH_2Z$, and $CZ_3$;

where Z is a halogen atom;

provided that, if both $R_1$ and $R_1'$ are H, then Y is other than COOH, COOMe or COOEt; and if Y=COOH, COOMe, or COOEt, then both $R_1$ and $R_1'$ are other than H.

2. The compound of claim 1 where at least one of $R_1$ and $R_1'$ is $NHCOCH_2Br$.

3. The compound of claim 1 where $R_2 = OCH_3$.

4. The compound of claim 1 where $R_4 = H$.

5. The compound of claim 1 where $X = H_2$.

6. The compound of claim 1 where $R_3$ is selected from the group consisting of $CH_2CH_2OCOCH_2Br$ and $CH_2COOH$.

7. The compound of claim 1 where $R_3 = COOH$.

8. The compound of claim 1 where at least one of $R_1$ and $R_1'$ is $NHCOCH_2Br$, $R_2$ is $OCH_3$, $R_4$ is H, and X is $H_2$.

9. The compound of claim 1 where said compound is 1-(4-bromoacetamidobenzyl)-5-methoxy-2-methylindole-3-acetic acid.

10. A pharmaceutical composition comprising a compound of claim 8 or its pharmaceutically acceptable salt.

11. A pharmaceutical composition comprising a compound of claim 9 or its pharmaceutically acceptable salt.

12. A method of inactivasting or affinity labeling antiinflammatory drug binding enzymes, enzymes containing prostaglandin binding sites or receptors for NSAIDs selected from 3α-HSD, prostaglandin transforming enzymes, PGH synthase and NSAID receptors comprising contacting said enzyme or receptor with a compound of claim 1.

13. A method of inactivasting or affinity labeling antiinflammatory drug binding enzymes, enzymes containing prostaglandin binding sites or receptors for NSAIDs selected from 3α-HSD, prostaglandin transforming enzymes, PGH synthase and NSAID receptors comprising contacting said enzyme or receptor with a compound of claim 8.

14. A method of inactivasting or affinity labeling antiinflammatory drug binding enzymes, enzymes containing prostaglandin binding sites or receptors for NSAIDs selected from 3α-HSD, prostaglandin transforming enzymes, PGH synthase and NSAID receptors comprising contacting said enzyme or receptor with a compound of claim 9.

15. The method of claim 12 wherein said enzyme is 3α-hydroxysteroid dehydrogenase.

16. The method of claim 12 wherein said enzyme is prostaglandin synthase.

17. The method of claim 12 wherein said enzyme is a prostaglandin dehydrogenase.

18. The method of claim 12 wherein said enzyme is an antiinflammatory drug binding enzyme.

19. A pharmaceutical composition comprising a compound of claim 1 or its pharmaceutically acceptable salt.

20. A compound of claim 1 where Y is selected from the group consisting of COH, $CH_2OCOCH_2Z$, $CH_2NHCOCH_2Z$ and $COCH_2Z$.

21. A compound of claim 20 where Z is Br.

22. A compound of claim 20 where $R_2$ is $OCH_3$, $R_1$ and $R_1'$ are independently selected from the group consisting of H and $NHCOCH_2Z$, and $R_4$ is selected from the group consisting of H and Z.

23. The compound of claim 1 where $R_1$ is H, $R_2$ is $OCH_3$, $R_3$ is $CH_2COOH$, $R_1'$ is $NHCOCH_2Br$ and $R_4$ is $H_2$.

24. A compound of claim 1 where one of $R_1$ and $R_1'$ is selected from the group consisting of $NHCOCH_2Z$, $OCOCH_2Z$ and $COPCH_2Z$.

25. A compound of claim 24 where Z is Br.

26. A compound of claim 24 where $R_2$ is $OCH_3$, $R_4$ is H, and Y is COOH.

* * * * *

UNITED STATES PATENT AND TRADEMARK OFFICE
CERTIFICATE OF CORRECTION

PATENT NO. : 5,187,187
DATED : February 16, 1993
INVENTOR(S) : Penning et al.

It is certified that error appears in the above-identified patent and that said Letters Patent is hereby corrected as shown below:

Column 1, Line 7 delete "Syntetase" and insert therefor --Synthetase--.

Column 2, Line 14 delete "*Prostaglandis*" and insert therefor --*Prostaglandins*--.

Column 2, Line 19 delete "Tai, H. H.," and insert therefor --Tai, H. -H.,--.

Column 2, Line 24 delete "been proposed Prostaglandin" and insert therefor --been proposed. Prostaglandin--.

Column 2, Line 25 delete "AND(P)+-linked" and insert therefor --NAD(P)$^+$-linked--.

Column 2, Line 26 delete "regioand" and insert therefor --region and--.

Column 2, Line 28 delete "by NSAIDS Inhibition" and insert therefor --by NSAIDS. Inhibition--.

Column 2, Line 32 delete "of rat liner" and insert therefor --of rat liver--.

Column 4, Line 1 delete "analyses NSAIDS" and insert therefor --analyses. NSAIDS--.

Column 5, Line 38, delete "$t_{½}$life" and insert therefor --$t_{½}$ life--.

Column 5, Line 62, delete "acetylating" and insert therefor --acylating--.

UNITED STATES PATENT AND TRADEMARK OFFICE
CERTIFICATE OF CORRECTION

PATENT NO. :   5,187,187
DATED      :   February 16, 1993
INVENTOR(S):   Penning et al.

It is certified that error appears in the above-identified patent and that said Letters Patent is hereby corrected as shown below:

Column 7, Lines 12-24 delete
"                                                                    "

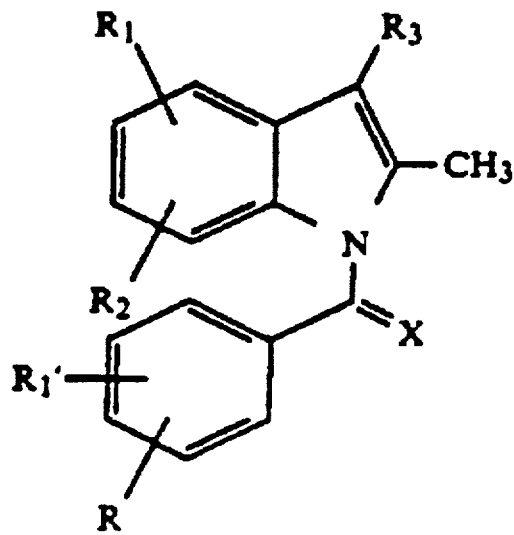

UNITED STATES PATENT AND TRADEMARK OFFICE
CERTIFICATE OF CORRECTION

PATENT NO. : 5,187,187  
DATED : February 16, 1993  
INVENTOR(S) : Penning et al.

Page 3 of 6

It is certified that error appears in the above-identified patent and that said Letters Patent is hereby corrected as shown below:

and insert

-- 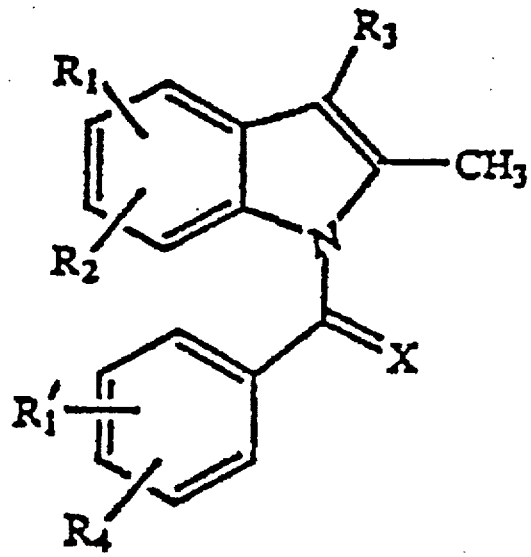 --

UNITED STATES PATENT AND TRADEMARK OFFICE
CERTIFICATE OF CORRECTION

PATENT NO. : 5,187,187
DATED : February 16, 1993
INVENTOR(S) : Penning et al.

It is certified that error appears in the above-identified patent and that said Letters Patent is hereby corrected as shown below:

Column 8, Line 47, delete "$t_{½}$life" and insert therefor --$t_{½}$ life--.

Column 8, Line 49, delete "$\mu$m" and insert therefor --$\mu M$--.

Column 8, Line 49, delete "$t_{½}$of" and insert therefor --$t_{½}$ of--.

Column 8, Line 50 delete "$\mu$m" and insert therefor --$\mu M$--.

Column 8, Line 51, delete "$t_{½}$of" and insert therefor --$t_{½}$ of--.

Column 8, Line 52, delete "$\mu$m" and insert therefor --$\mu M$--.

Column 8, Line 52, delete "$t_{½}$of" and insert therefor --$t_{½}$ of--.

Column 13, Line 1 delete "derviative" and insert therefor --derivative--.

Column 13, Line 59, delete "I-" and insert therefor --1- --.

Column 14, Line 53 delete "pd/C" and insert therefor --Pd/C--.

Column 14, Line 68 delete "$M^1$," and insert therefor --$M^{-1}$--.

UNITED STATES PATENT AND TRADEMARK OFFICE
CERTIFICATE OF CORRECTION

PATENT NO. : 5,187,187
DATED : February 16, 1993
INVENTOR(S) : Penning et al.

It is certified that error appears in the above-identified patent and that said Letters Patent is hereby corrected as shown below:

Column 15, Line 26 delete "$M^1$," and insert therefor --$M^1$--.

Column 16, Line 6, delete "(VI)" and insert therefor --(VII)--.

Column 16, Line 7, delete "Were" and insert therefor --were--.

Column 16, Line 13 delete "$AND^+in$" and insert therefor --$NAD^+$ in--.

Column 16, Line 12, delete "nM" and insert therefor --nm--.

Column 16, Line 22 delete "$3\mu$-HSD" and insert therefor --$3\alpha$-HSD--.

Column 16, Line 27 delete "$AND^+$" and insert therefor --$NAD^+$--.

Column 16, Line 64, delete "$N(ME)_2$" and insert therefor --$N(Me)_2$--.

Column 17, Line 30 delete "inactivasting" and insert therefor --inactivating--.

Column 17, Line 37 delete "inactivasting" and insert therefor --inactivating--.

Column 18, Line 5 delete "inactivasting" and insert therefor --inactivating--.

Column 18, Line 23 delete "of COH," and insert therefor --of COOH--.

UNITED STATES PATENT AND TRADEMARK OFFICE
CERTIFICATE OF CORRECTION

PATENT NO. :   5,187,187
DATED      :   February 16, 1993
INVENTOR(S):   Penning et al.

It is certified that error appears in the above-identified patent and that said Letters Patent is hereby corrected as shown below:

Column 18, Line 35 delete "and COPCH$_2$Z." and insert therefor -- COCH$_2$Z.--.

Column 6, Lines 50-55, delete
"

and insert therefor
--

Signed and Sealed this

Fifteenth Day of March, 1994

Attest:

BRUCE LEHMAN

Attesting Officer      Commissioner of Patents and Trademarks